(12) United States Patent
Shimada et al.

(10) Patent No.: US 8,101,162 B2
(45) Date of Patent: Jan. 24, 2012

(54) HAIR GROWTH COMPOSITION

(75) Inventors: Maki Shimada, Kawasaki (JP);
Yoshinobu Takino, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 465 days.

(21) Appl. No.: 12/330,054

(22) Filed: Dec. 8, 2008

(65) Prior Publication Data

US 2009/0131337 A1 May 21, 2009

Related U.S. Application Data

(63) Continuation of application No. PCT/JP2007/061692, filed on Jun. 5, 2007.

(30) Foreign Application Priority Data

Jun. 8, 2006 (JP) ................................. 2006-159323

(51) Int. Cl.
*A61K 8/64* (2006.01)
*A61K 38/05* (2006.01)

(52) U.S. Cl. ................... 424/70.1; 424/70.14; 514/20.7; 514/21.91

(58) Field of Classification Search .......................... None
See application file for complete search history.

(56) References Cited

FOREIGN PATENT DOCUMENTS

| | | |
|---|---|---|
| JP | 63-96106 | 4/1988 |
| JP | 5-301814 | 11/1993 |
| JP | 6-40844 | 2/1994 |
| JP | 2002-363035 | 12/2002 |
| JP | 2004-99599 | 4/2004 |
| WO | WO 02/056849 A1 | 7/2002 |

OTHER PUBLICATIONS

Machine translation of JP 5-301814 (Nov. 16, 1993).*
Fragance Journal, No. 80, 1986, p. 109-114 (with partial English translation).
Ming Li, et al., "Minoxidil-Induced Hair Growth is Mediated by Adenosine in Cultured Dermal Papilla Cells: Possible Involvement of Sulfonylurea Receptor 2B as a Target of Minoxidil", J. Invest. Dermatol., vol. 117, 2001, pp. 1594-1600.
Fragance Journal, No. 6, 2005, pp. 13-18 (with English Abstract).
Fragance Journal, No. 3, 2001, pp. 39-46 (with English Abstract).

* cited by examiner

*Primary Examiner* — Jeffrey E Russel
(74) *Attorney, Agent, or Firm* — Oblon, Spivak, McClelland, Maier & Neustadt, L.L.P.

(57) ABSTRACT

The present invention provides a hair growth agent having novel action mechanism and a hair growth composition containing the agent. Specifically, the present invention provides a novel hair growth composition containing one or more kinds of epsilon-N-(gamma-glutamyl)lysine or a salt thereof.

7 Claims, No Drawings

HAIR GROWTH COMPOSITION

CROSS REFERENCES TO RELATED APPLICATIONS

This application is a continuation of International Patent Application No. PCT/JP2007/061692, filed on Jun. 5, 2007, and claims priority to Japanese Patent Application No. 2006-159323, filed on Jun. 8, 2006, both of which are incorporated herein by reference in their entireties.

BACKGROUND OF THE INVENTION

1. Field of the Invention

The present invention relates to hair growth agents and hair growth compositions. The present invention further relates to methods for growing hair.

2. Discussion of the Background

Alopecia is developed by a complicated entanglement of genetic factors, influence of male hormones, physical factors such as decline of blood flow to the hair follicle, aging and the like, as well as increased stress, change of lifestyle and the like.

Conventional hair growth agents, for example, hair growth agents containing glyceryl pentadecanoate, adenosine, minoxidil and the like as main components mainly aim at nutritional support, promoted blood circulation, scalp improvement, cell activating effect and the like.

Glyceryl pentadecanoate is known to function as an efficient energy supply material for the hair follicle with decreased level of energy metabolism, and promote hair growth (FRAGRANCE JOURNAL, No. 80, 1986, p. 109-114). However, it does not necessarily provide a satisfactory hair growth effect.

Adenosine and minoxidil are known to act on hair papilla cell, induce production of cell growth factor and activate hair follicle cells (see J. Invest. Dermatol., 117, 2001, p. 1594-1600; FRAGRANCE JOURNAL, No. 6, 2005, p. 13-18; and FRAGRANCE JOURNAL, No. 3, 2001, p. 39-46). However, they do not necessarily provide a satisfactory hair growth effect, either.

On the other hand, a cosmetic containing epsilon-N-(gamma-glutamyl)lysine or a salt thereof is known (JP-A-5-301814). However, the object thereof is what is called a "beautiful skin effect".

Conventional hair growth agents and active ingredients contained therein do not have a sufficiently satisfactory hair growth effect, and a novel hair growth composition having a new action mechanism has been greatly desired.

SUMMARY OF THE INVENTION

An object of the present invention is to provide a novel hair growth composition having a novel action mechanism.

The present inventors have conducted intensive studies and found that epsilon-N-(gamma-glutamyl)lysine and a salt thereof proliferate hair papilla cells and human epidermal keratinocytes and afford a hair growth effect, which resulted in the completion of the present invention. In addition, they have found that human epidermal keratinocytes can be proliferated by combining the hair growth agent of the present invention and a particular amino acid, which affords a more superior hair growth effect.

Accordingly, the present invention encompasses the following embodiments.

(1) A hair growth agent consisting of epsilon-N-(gamma-glutamyl)lysine or a salt thereof.

(2) A hair growth composition comprising epsilon-N-(gamma-glutamyl)lysine or a salt thereof.

(3) A hair growth composition comprising epsilon-N-(gamma-glutamyl)lysine or a salt thereof, and one or more kinds selected from amino acids selected from the following first amino acid group and salts thereof:
first amino acid group: glutamine, leucine.

(4) A hair growth composition comprising epsilon-N-(gamma-glutamyl)lysine or a salt thereof, one or more kinds selected from amino acids selected from the following first amino acid group and salts thereof and one or more kinds selected from amino acids selected from the following second amino acid group and salts thereof:
first amino acid group: glutamine, leucine
second amino acid group: lysine, isoleucine, asparagine, arginine, glutamic acid.

(5) The hair growth composition of the above-mentioned (3) or (4), wherein the ratio (B/A) of the mass of first amino acid group (Component B) to the mass of epsilon-N-(gamma-glutamyl)lysine or a salt thereof (Component A) is 0.015-700.

(6) The hair growth composition of the above-mentioned (4) or (5), wherein the ratio (C/A) of the mass of second amino acid group (Component C) to the mass of epsilon-N-(gamma-glutamyl)lysine or a salt thereof (Component A) is 0.0005-200.

(7) Use of epsilon-N-(gamma-glutamyl)lysine or a salt thereof for growing hair.

(8) A method of growing hair, comprising applying a composition comprising epsilon-N-(gamma-glutamyl)lysine or a salt thereof to the skin.

(9) A method of growing hair, comprising applying, to the skin, a composition comprising epsilon-N-(gamma-glutamyl)lysine or a salt thereof, and one or more kinds selected from amino acids selected from the following first amino acid group and salts thereof:
first amino acid group: glutamine, leucine.

(10) A method of growing hair, comprising applying, to the skin, a composition comprising epsilon-N-(gamma-glutamyl)lysine or a salt thereof, one or more kinds selected from amino acids selected from the following first amino acid group and salts thereof and one or more kinds selected from amino acids selected from the following second amino acid group and salts thereof:
first amino acid group: glutamine, leucine
second amino acid group: lysine, isoleucine, asparagine, arginine, glutamic acid

(11) The method of growing hair, of the above-mentioned (9) or (10), wherein the ratio (B/A) of the mass of first amino acid group (Component B) to the mass of epsilon-N-(gamma-glutamyl)lysine or a salt thereof (Component A) is 0.015-700.

(12) The method of growing hair, of the above-mentioned (10) or (11), wherein the ratio (C/A) of the mass of second amino acid group (Component C) to the mass of epsilon-N-(gamma-glutamyl)lysine or a salt thereof (Component A) is 0.0005-200.

In the present specification, the "mass of component A" means a mass as glutamyllysine, and when glutamyllysine salt is used as component A, it can be used after appropriate conversion.

Similarly, in the present specification, the "mass of component B" and "mass of component C" mean the mass of amino acid in a free form to be contained as component B and component C, and when a salt thereof is used, it can be used after appropriate conversion.

The present invention can provide a hair growth composition that stimulates proliferation of hair follicle cell such as hair matrix cell and hair papilla cell.

DETAILED DESCRIPTION OF THE PREFERRED EMBODIMENTS

The hair growth composition of the present invention is sequentially explained in the following.

Epsilon-N-(gamma-glutamyl)lysine (hereinafter to be abbreviated as glutamyllysine) to be used in the present invention is dipeptide (isopeptide) having a structure of the following structural formula (I).

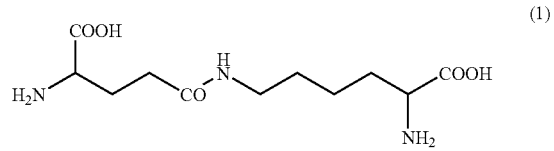

(1)

As a method of obtaining a glutamyllysine of this invention, the method described in Biochemistry, vol. 2, p. 740-745 (1963), JP-A-51-105014 and the like can be used.

Glutamyllysine obtained as mentioned above is an odorless white powder, which is hardly soluble or insoluble in various organic solvents such as methanol, ethanol, acetone and the like, and soluble in alkaline water, acidic water and the like.

The above-mentioned glutamyllysine can be used in the form of a salt. Using glutamyllysine in the form of a salt, it can be dissolved not only in the aforementioned alkaline water and acidic water but also neutral water.

Examples of such salt form include alkali metal salts such as potassium, sodium and the like, alkaline earth metal salts such as calcium, magnesium and the like, organic amine salts such as ammonium, triethanolamine and the like, basic amino acid salts such as lysine, arginine and the like, mineral acid salts such as hydrochloric acid, sulfuric acid and the like, organic acid salts such as acetic acid, citric acid and the like, and the like. In consideration of the solubility, safety and the like, alkali metal salts, alkaline earth metal salts and basic amino acid salts are preferable, alkali metal salts and alkaline earth metal salts are more preferable, and alkali metal salts are particularly preferable.

In the following, epsilon-N-(gamma-glutamyl)lysine or a salt thereof is described as component A.

When epsilon-N-(gamma-glutamyl)lysine or a salt thereof is used in combination with one or more kinds selected from amino acids selected from the first amino acid group and salts thereof, the cell proliferation effect of glutamyllysine can be enhanced without inhibiting the normal cell growth.

In the following, the first amino acid group is described as component B. The first amino acid group consists of glutamine and leucine. These amino acids may be in a free form or in the form of a salt. Any of the optical isomers such as L form and D form can be used, and racemate (D and L forms) can also be used. Only one kind can be used as component B, or a mixture of two or more kinds can be used as a component B.

When used as a composition, the amount of component B to be used in the present invention is not limited. However, the mass of component B relative to the mass of component A (B/A) is preferably 0.015-700. When the ratio is less than 0.015, the cell proliferation rate sometimes may not be increased as expected, and when the ratio exceeds 700, it may sometimes inhibit the cell proliferation rate. Since the cell proliferation rate can be efficiently enhanced, the lower limit is more preferably 0.1, still more preferably 0.2, still more preferably 2, especially preferably 4, and particularly preferably 4.8. On the other hand, since the cell proliferation rate is not inhibited, the upper limit is more preferably 300, still more preferably 250, further more preferably 125, especially preferably 60, and particularly preferably 35.

Particularly, since the effect of glutamyllysine can be enhanced without inhibiting the normal cell growth, glutamine or a salt thereof and leucine or a salt thereof are preferably used in combination. In this case, the ratio of the amount of glutamine or a salt thereof and leucine or a salt thereof is preferably 1:2-250:1, more preferably 3:1-60:1, and further preferably 5:1-25:1, by mass ratio.

Furthermore, when one or more kinds of amino acids selected from the second amino acid group and salts thereof are used in combination, the cell proliferation effect can be further enhanced. In the following, the second amino acid group is described as component C. The second amino acid group consists of lysine, isoleucine, asparagine, arginine and glutamic acid. These amino acids may be in a free form or in the form of a salt. Any of the optical isomers such as L form and D form can be used, and racemate (D and L forms) can also be used. Only one kind can be used as component C, or a mixture of two or more kinds can be used as a component C. Since the cell proliferation rate is particularly remarkable, lysine and isoleucine are preferable, and lysine is particularly preferable.

While the amount of component C to be used in the present invention is not limited, the mass of component C relative to the mass of component A (C/A) is preferably 0.0005-200. When the ratio is less than 0.0005, it sometimes hardly influences enhancement of the cell proliferation effect, and when the ratio exceeds 200, it sometimes inhibits the cell proliferation rate. Since the cell can be activated, the lower limit is more preferably 0.001, further preferably 0.01, still further preferably 0.015, especially preferably 0.03, and particularly preferably 0.07. On the other hand, since the cell proliferation rate is not inhibited, the upper limit is more preferably 160, still more preferably 120, further more preferably 60, especially preferably 30, and particularly preferably 15.

The hair growth agent of the present invention can be used as a hair growth composition by dissolving the agent in a solvent. Specific examples of the solvent to be used include lower alcohol such as ethanol, isopropyl alcohol and the like; polyvalent alcohol such as glycerol, propylene glycol, butylene glycol and the like; water and the like. The amount of the solvent to be used can be appropriately selected according to the composition of the hair growth composition.

The content of component A in the hair growth composition is preferably within the range of 0.0001-10 mass %. When the content is less than 0.0001 mass %, the hair growth effect is sometimes poor, and when it exceeds 10 mass %, an increase in the effect cannot substantially be expected and the pores on the skin may be filled with the precipitate of component A. Since the hair growth effect is effectively provided, the lower limit more preferably 0.0005 mass %, further preferably 0.0007 mass %, and particularly preferably 0.001 mass %. Since the effect can be provided without filling pores, the upper limit value is more preferably 5 mass %, further preferably 2 mass %, and particularly preferably 0.1 mass %.

In addition, the hair growth composition of the present invention can appropriately contain various components generally used for pharmaceutical products, cosmetics and the like, to the extent the effect of the present invention is not inhibited. Specifically, aqueous component, oily component, powder component, surfactant, moisturizer, thickener, colorant, fragrant material, antioxidant, PH adjuster, chelator, preservative, or UV protective agent, anti-inflammatory agent, whitening agent, anti-aging agent, blood flow promoting agent, write hair preventive agent and the like can be added.

While the form of the hair growth composition of the present invention is not particularly limited, specific examples include liquid, paste, gel, foam, cream, solid and the like. Since the hair growth effect can be efficiently provided, liquid and gel are preferable.

For testing the hair growth effect of the present invention, a test method of measuring the cell proliferation rate of hair papilla cells and hair matrix cells, as the one described in "FRAGRANCE JOURNAL extra edition, No. 13, 1994, p. 105-106", has been employed. Particularly, the test method of the present invention is extremely useful in that it can conveniently and rapidly test the hair growth effect utilizing hair papilla cells and human epidermal keratinocytes (substitute for hair matrix cells). Particularly, a test method based on a human epidermal keratinocyte proliferation test (amino acid-free medium) uses a medium completely free of amino acid as a nutrient source, and is an extremely useful test method which enables convenient observation of cell proliferation in the scalp during the catagen phase.

EXAMPLES

The present invention is explained in detail in the following by referring to Examples, which are not to be construed as limitative.

The test methods are now explained.
Hair Papilla Cell Proliferation Test.

(1) Using a proliferation medium PCGM: Papilla Cell Growth Medium (purchased from TOYOBO CO., LTD., TPGM-250), hair papilla cells were plated to a cell seeding density of $1.0 \times 10^4$ cells/well in a 96 well plate.

(2) After culturing at 37° C. in a 5% carbon dioxide gas ($CO_2$) atmosphere for one day, the medium was removed, and the cells were washed with an evaluation medium used for cell proliferation tests, i.e., DMEM (Dulbecco's Modified Eagle's Medium) medium containing 1% FCS (fetal bovine serum). Then, various test components were dissolved in a similar evaluation medium and added to various concentrations (• mol/l).

(3) Subsequently, the cells were further cultured at 37° C. in a 5% carbon dioxide gas ($CO_2$) atmosphere for 2 days, and the hair papilla cell proliferation rate was measured by the MTT method.

(4) The relative evaluation value was calculated based on the rate obtained using a medium free of various hair growth components as 100, and the value was taken as the proliferation rate.
Human Epidermal Keratinocyte Proliferation Test.

(1) Using a serum-free proliferation medium HuMedia-KB2 (purchased from KURABO INDUSTRIES LTD., KK-2350S) added with a proliferation additive HuMedia-KG (purchased from KURABO INDUSTRIES LTD., KK-6150), human epidermal keratinocytes were plated to a cell seeding density of $2.0 \times 10^4$ cells/well in a 96 well plate.

(2) After culturing at 37° C. in a 5% carbon dioxide gas ($CO_2$) atmosphere for one day, the medium was removed, and the cells were washed with an evaluation medium used for cell proliferation tests, i.e., MCDB153 medium. Then, various test components were dissolved in a similar evaluation medium and added to various concentrations (• mol/l).

(3) Subsequently, the cells were further cultured at 37° C. in a 5% carbon dioxide gas ($CO_2$) atmosphere for 2 days, and the human epidermal keratinocyte proliferation rate was measured by the MTT method.

(4) The relative evaluation value was calculated based on the rate obtained using a medium free of various hair growth components as 100, and the value was taken as the proliferation rate.
<Human Epidermal Keratinocyte Proliferation Test (Amino Acid-Free Medium)>

(1) Using a serum-free proliferation medium HuMedia-KB2 (purchased from KURABO INDUSTRIES LTD., KK-2350S) added with a proliferation additive HuMedia-KG (purchased from KURABO INDUSTRIES LTD., KK-6150), human epidermal keratinocytes were plated to a cell seeding density of $2.0 \times 10^4$ cells/well in a 96 well plate.

(2) After culturing at 37° C. in a 5% carbon dioxide gas ($CO_2$) atmosphere for one day, the medium was removed, and the cells were washed with an evaluation medium used for cell proliferation tests, i.e., MCDB153 medium from which all amino acids had been removed (amino acid-free medium). Then, various hair growth compositions as shown in Table 2 dissolved in similar evaluation media were added.

(3) Subsequently, the cells were further cultured at 37° C. in a 5% carbon dioxide gas ($CO_2$) atmosphere for 2 days, and the human epidermal keratinocyte proliferation rate was measured by the MTT method.

(4) The relative evaluation value was calculated based on the rate obtained using a medium free of various amino acids and various hair growth components as 100, and the value was taken as the proliferation rate.

Example 1

Comparative Examples 1-2

The compounds shown in Table 1 were subjected to a human epidermal keratinocyte proliferation test and a hair papilla cell proliferation test at various concentrations.

TABLE 1

| | | hair papilla cell | | keratinocyte | |
|---|---|---|---|---|---|
| | test component | concentration used | proliferation rate (%) | concentration used | proliferation rate (%) |
| Ex. 1 | glutamyllysine | 100 · mol/L | 124 | 50 · mol/L | 131 |
| Com. Ex. 1 | adenosine | 100 · mol/L | 99 | 50 · mol/L | 118 |
| Com. Ex. 2 | minoxidil | 100 · mol/L | 113 | 50 · mol/L | 117 |
| blank value | none | none | 100 | none | 100 |

From the aspects of proliferation of hair papilla cells and human epidermal keratinocytes, it has been clarified that glutamyllysine has a proliferation effect equal to or greater than that of known hair growth components adenosine and minoxidil.

Examples 2-14

The compositions of Examples 2-14 were prepared and subjected to a human epidermal keratinocyte proliferation test (amino acid-free medium).

TABLE 2

| | first amino acid group | second amino acid group | | | | | | human epidermal keratinocyte proliferation rate (%) |
|---|---|---|---|---|---|---|---|---|
| | glutamyllysine | glutamine | leucine | lysine | isoleucine | asparagine | arginine | glutamic acid | |
| Ex. 2 | 27.5 | — | — | — | — | — | — | — | 127 |
| Ex. 3 | 27.5 | 876 | 65.5 | — | — | — | — | — | 148 |
| Ex. 4 | 27.5 | 876 | 65.5 | 14.7 | — | — | — | — | 171 |
| Ex. 5 | 27.5 | 876 | 65.5 | — | 1.97 | — | — | — | 150 |
| Ex. 6 | 27.5 | 876 | 65.5 | — | — | 13.2 | — | — | 134 |
| Ex. 7 | 27.5 | 876 | 65.5 | — | — | — | 193 | — | 156 |
| Ex. 8 | 27.5 | 876 | 65.5 | — | — | — | — | 14.7 | 139 |
| Ex. 9 | 13.8 | 876 | 65.5 | — | — | — | — | — | 163 |
| Ex. 10 | 13.8 | 876 | 65.5 | 14.7 | — | — | — | — | 190 |
| Ex. 11 | 13.8 | 876 | 65.5 | — | 1.97 | — | — | — | 174 |
| Ex. 12 | 13.8 | 876 | 65.5 | — | — | 13.2 | — | — | 179 |
| Ex. 13 | 13.8 | 876 | 65.5 | — | — | — | 193 | — | 162 |
| Ex. 14 | 13.8 | 876 | 65.5 | — | — | — | — | 14.7 | 185 |
| blank | — | — | — | — | — | — | — | — | 100 |

Glutamyllysine, which is the hair growth agent of the present invention, provides an enhanced proliferation effect on human epidermal keratinocytes by the addition of the first amino acid group. Additionally, it is clear that the proliferation effect on human epidermal keratinocytes is further enhanced by the addition of the second amino acid group.

Formulation Example 1

A hair growth lotion was prepared with the composition shown in the following Table 3.

TABLE 3

| hair growth lotion | |
|---|---|
| | wt % |
| ethanol | 50 |
| glutamyllysine | 0.1 |
| L-glutamine | 1.5 |
| L-leucine | 0.3 |
| L-lysine | 0.3 |
| L-arginine | 0.5 |
| tocopherol acetate | 0.5 |
| purified water | 46.8 |
| | 100 |

INDUSTRIAL APPLICABILITY

A hair growth agent and a hair growth composition having novel action mechanism can now be provided.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of growing hair, comprising applying a composition comprising epsilon-N-(gamma-glutamyl)lysine or a salt thereof to the skin of a scalp of a subject in need thereof.

2. A method of growing hair, comprising applying, to the skin of a scalp of a subject in need thereof, a composition comprising epsilon-N-(gamma-glutamyl)lysine or a salt thereof, and one or more kinds selected from amino acids selected from the following first amino acid group and salts thereof:
first amino acid group: glutamine, and leucine.

3. A method of growing hair, comprising applying, to the skin of a scalp in a subject in need thereof, a composition comprising epsilon-N-(gamma-glutamyl)lysine or a salt thereof, one or more kinds selected from amino acids selected from the following first amino acid group and salts thereof and one or more kinds selected from amino acids selected from the following second amino acid group and salts thereof (Component C):
first amino acid group: glutamine, and leucine
second amino acid group: lysine, isoleucine, asparagine, arginine, and glutamic acid.

4. The method of growing hair of claim 2, wherein the ratio (B/A) of the mass of first amino acid group (Component B) to the mass of epsilon-N-(gamma-glutamyl)lysine or a salt thereof (Component A) is 0.015-700.

5. The method of growing hair of claim 3, wherein the ratio (B/A) of the mass of first amino acid group (Component B) to the mass of epsilon-N-(gamma-glutamyl)lysine or a salt thereof (Component A) is 0.015-700.

6. The method of growing hair of claim 3, wherein the ratio (C/A) of the mass of second amino acid group (Component C) to the mass of epsilon-N-(gamma-glutamyl)lysine or a salt thereof (Component A) is 0.0005-200.

7. The method of growing hair of claim 5, wherein the ratio (C/A) of the mass of second amino acid group (Component C) to the mass of epsilon-N-(gamma-glutamyl)lysine or a salt thereof (Component A) is 0.0005-200.

* * * * *